United States Patent
Omura et al.

(10) Patent No.: US 7,192,742 B2
(45) Date of Patent: Mar. 20, 2007

(54) FO-6979 SUBSTANCES AND PROCESS FOR PRODUCING THE SAME

(75) Inventors: Satoshi Omura, Tokyo (JP); Hiroshi Tomoda, Tokyo (JP)

(73) Assignees: Gakkou Houjin Kitasato Gakuen, Tokyo (JP); Japan Society for the Promotion of Science, Tokyo (JP)

( * ) Notice: Subject to any disclaimer, the term of this patent is extended or adjusted under 35 U.S.C. 154(b) by 497 days.

(21) Appl. No.: 10/343,990

(22) PCT Filed: Mar. 19, 2002

(86) PCT No.: PCT/JP02/02590

§ 371 (c)(1),
(2), (4) Date: May 28, 2003

(87) PCT Pub. No.: WO02/074792

PCT Pub. Date: Sep. 26, 2002

(65) Prior Publication Data

US 2003/0195146 A1    Oct. 16, 2003

(30) Foreign Application Priority Data

Mar. 21, 2001    (JP)    .............................. 2001-080388

(51) Int. Cl.
  C12P 21/04    (2006.01)
  C12N 1/20    (2006.01)
  C07K 7/64    (2006.01)
  A61K 38/00    (2006.01)

(52) U.S. Cl. ................. 435/71.2; 435/71.1; 435/252.1; 514/8; 514/11; 530/317

(58) Field of Classification Search ............... 435/71.1, 435/71.2, 252.1; 514/219, 8, 11; 530/317
See application file for complete search history.

(56) References Cited

U.S. PATENT DOCUMENTS 6,902,925 B2 * 6/2005 Omura et al. ............ 435/256.8

FOREIGN PATENT DOCUMENTS

JP    11-279195    10/1999

OTHER PUBLICATIONS

Kuzma et al., J. Mass Spectrom. 2001; 36: 1108-1115.*
Machine translation of JP 11-279195 (entire document) obtained from www4.ipdl.nipi.go.jp/cgo-bin/tran_web_cgi_ejje on Apr. 14, 2006.*
K. Mochizuki et al., "The structures of bioactive cyclodepsipeptides, Beauveriolides I and II, metabolites of entomophathogenic Fungi Beauveria sp.", Bull.Chem.Soc.Jpn., 1993, 66, pp. 3041 to 3046.
I. Namatame et al., "Beauveriolides, specific inhibitors of lipid droplet formation in mouse macrophages, produced by Beauveria sp. FO-6979", The Journal of Antibiotics, 1999, 52(1), pp. 1 to 6.
J. Alexandr et al., "Beauverolides L and La from beauveria tenella and paecilomyces fumosoroseus", Phytochemistry, 1994, 37(5), pp. 1301 to 1303.
J.F. Elsworth et al., Cyclodepsipeptides from Beauveria bassiana. Part 2. Beauverolides A to F and their relationship to Isarolide, J. Chem. Soc. Perkin Trans. I, 1980, pp. 1795 to 1799.
J. F. Grove et al., Cyclodepsipeptides from Beauveria bassiana. Part 3. The isolation of Beauverolides Ba, Ca, Ja and Ka, J. Chem.Soc. Perkin Trans. I, 1980. 12, pp. 2878 to 2880.
J. F. Elsworth et al., "Cyclodepsipeptides from Beauveria bassiana Bals. Part 1. Beauverolides H and I", J. Chem. Soc. Perkin Trans. I, 1977, 3, pp. 270 to 273.
K. Marek et al., Sequencing of new beauverolides by highperformance liquid chromatography and mass spectrometry, J. Mass. Spectrom., Sep 2001, 36, pp. 1108 to 1115.

* cited by examiner

*Primary Examiner*—Irene Marx
*Assistant Examiner*—Susan Hanley
(74) *Attorney, Agent, or Firm*—Young & Thompson (57)    ABSTRACT

(*Beauveria*) sp. FO-6979 (FERM BP-6681), which belongs to the genus *Beauveria* and is capable of producing FO-6979-M0, -M1, -M2, -M3 and -M4 substances, is cultured in a medium to thereby accumulate the FO-6979-M0, -M1, -M2, -M3 and -M4 substances in the liquid culture medium. Then the FO-6979-M0, -M1, -M2, -M3 and -M4 substances are collected from the culture medium. The substances thus obtained are less toxic, specifically inhibit acyl-Coenzyme A: cholesterol acyltransferase, and inhibit the formation of oil droplets in macrophages. Owing to these characteristics, the above substances are useful in preventing and treating human diseases caused by cholesterol accumulation.

25 Claims, 5 Drawing Sheets

FO-6979 SUBSTANCES AND PROCESS FOR PRODUCING THE SAME

BACKGROUND OF THE INVENTION

1. Field of the Invention

The present invention relates to FO-6979 substances having inhibitory action against acyl-CoA: cholesterol acyltransferase and a process for production thereof.

In the present invention, FO-6979 substances include FO-6979-M0 substance, FO-6979-M1 substance, FO-6979 M2 substance, FO-6979-M3 substance and FO-6979-M4 substance.

2. Description of the Related Art

Recently, diseases caused by accumulation of cholesterol such as hyperlipidemia and arteriosclerosis of adults accompanied by improvement of food eating habit are brought into question as the modern disease. Cholesterol is converted to cholesterol ester by acyl group transfer of coenzyme A (hereinafter abbreviated as CoA) and accumulated in cells and blood lipoprotein. The enzyme which catalyzes such acyl group transfer reaction is acyl-CoA: cholesterol O-acyltransferase (hereinafter designates as acyl-CoA cholesterol acyltransferase), and is deeply involved in absorption of cholesterol from the intestinal tract, formation of lipoprotein in the liver and formation of foam cells in the coronary artery (Sliskovic, D. R. and White, A. D. Trend. Pharm. Sci. 12, 194–199, 1991).

Consequently, substance inhibiting acyl-CoA cholesterol acyltransferase may be useful for treatment of such diseases.

SUMMARY OF THE INVENTION

Development of drugs based on such mechanism of action is strongly desired, and under such circumstances, providing substance having inhibitory action against acyl-CoA cholesterol acyltransferase is to provide new preventive and therapeutic methods for adult diseases such as hyperlipidemia and arteriosclerosis caused thereby and is useful.

We have continued studies on metabolites produced by microorganisms, and as a result, we have found to produce substance having inhibitory action against acyl-CoA cholesterol acyltransferase in the cultured medium of the microorganism strain FO-6979 isolated from soil. We had designated the substance as FO-6979 substance and had filed the application of the invention of the substance under the title as novel FO-6979 substance and a process for production thereof (JP-A-11-279195).

We have further continued studies on metabolites of the strain FO-6979 and newly found that substances having inhibitory action against acyl-CoA cholesterol acyltransferase in the cultured medium of the microorganism strain FO-6979. Subsequently, the substances having inhibitory action against acyl-CoA cholesterol acyltransferase were isolated from the cultured mass and purified, as a result, since the substances having such chemical structures were not known previously, the substances were designated as FO-6979-M0 substance, FO-6979-M1 substance, FO-6979-M2 substance, FO-6979-M3 substance and FO-6979-M4 substance (hereinafter sometimes designates as FO-6979 substances or FO-6979-M0 substance, -M1 substance, -M2 substance, -M3 substance and -M4 substance).

The present invention has completed according to such knowledge, consequently, the present substance has inhibitory action against acyl-CoA cholesterol acyltransferase and inhibits lipid droplet formation in the macrophages, and as a result, it is highly expected to prevent adult diseases such as hyperlipidemia and arteriosclerosis based on it.

The present invention provides novel FO-6979-M0 substance, which is a compound represented by the following formula [I]

The present invention further provides a process for production of novel FO-6979-M0 substance comprising culturing a microorganism belonging to genus *Beauveria* and having ability to produce FO-6979-M0 substance in a medium, accumulating FO-6979-M0 substance in the cultured liquid medium and isolating FO-6979-M0 substance from said cultured mass.

*Beauveria* sp. FO-6979 FERM BP-6681 can be used as the microorganism having ability to produce FO-6979-M0 substance of the present invention, and the obtained substance has inhibitory actions against acly-CoA cholesterol acyltransferase, formation of cholesterylesters and lipid droplet formation in macrophages.

The present invention further provides novel FO-6979-M1 substance, which is a compound represented by the following formula [II].

The present invention further provides a process for production of novel FO-6979-M1 substance comprising culturing a microorganism belonging to genus *Beauveria* and having ability to produce FO-6979-M1 substance in a medium, accumulating FO-6979-M1 substance in the cultured liquid medium and isolating FO-6979-M1 substance from said cultured mass.

*Beauveria* sp. FO-6979 FERM BP-6681 can be used as the microorganism having ability to produce FO-6979-M1 substance of the present invention, and the obtained substance has inhibitory actions against acyl-CoA cholesterol acyltransferase, formation of cholesterylesters and lipid droplet formation in macrophages.

The present invention further provides novel FO-6979-M2 substance, which is a compound represented by the following formula [III]

[III]

[V]

The present invention further provides a process for production of novel FO-6979-M2 substance comprising culturing a microorganism belonging to genus *Beauveria* and having ability to produce FO-6979-M2 substance in a medium, accumulating FO-6979-M2 substance in the cultured liquid medium and isolating FO-6979-M2 substance from said cultured mass.

*Beauveria* sp. FO-6979 FERM BP-6681 can be used as the microorganism having ability to produce FO-6979-M2 substance of the present invention, and the obtained substance has inhibitory actions against acyl-CoA cholesterol acyltransferase, formation of cholesterylesters and lipid droplet formation in macrophages.

The present invention further provides novel FO-6979-M3 substance, which is a compound represented by the following formula [IV]

[IV]

The present invention further provides a process for production of novel FO-6979-M3 substance comprising culturing a microorganism belonging to genus *Beauveria* and having ability to produce FO-6979-M3 substance in a medium, accumulating FO-6979-M3 substance in the cultured liquid medium and isolating FO-6979-M3 substance from said cultured mass.

*Beauveria* sp. FO-6979 FERM BP-6681 can be used as the microorganism having ability to produce FO-6979-M3 substance of the present invention, and the obtained substance has inhibitory actions against acyl-CoA cholesterol acyltransferase, formation of cholesterylesters and lipid droplet formation in macrophages.

The present invention further provides novel FO-6979-M4 substance, which is a compound represented by the following formula [V]

The present invention further provides a process for production of novel FO-6979-M4 substance comprising culturing a microorganism belonging to genus *Beauveria* and having ability to produce FO-6979-M4 substance in a medium, accumulating FO-6979-M4 substance in the cultured liquid medium and isolating FO-6979-M4 substance from said cultured mass.

*Beauveria* sp. FO-6979 FERM BP-6681 can be used as the microorganism having ability to produce FO-6979-M4 substance of the present invention, and the obtained substance has inhibitory actions against acyl-CoA cholesterol acyltransferase, formation of cholesterylesters and lipid droplet formation in macrophages.

The microorganism having ability to produce the above-described FO-6979-M0 substance, -M1 substance, -M2 substance, -M3 substance and -M4 substance (hereinafter designates as "FO-6979 substance producing microorganism") belongs to genus *Beauveria* sp., and *Beauveria* sp. FO-6979 strain isolated from soil by the inventors of the present invention is an example of the strain which can be used most effectively in the present invention. Taxonomical properties of the strain FO-6979 are as follows.

1. Taxonomical Properties

This strain has good growth on media such as potato glucose agar, cornmeal agar, malt extract agar and Miura agar with good growth of conidiospores. In addition, good growth on yeast extract soluble starch agar medium is observed, but no bearing of conidiospores is observed. Microscopic observation of conidiospores grown on the cornmeal agar medium indicates transparent hyphae with septa. The conidiophores were born directly from vegetable hyphae or through short branches. Basal part of conidiospore is spherical or ventricose in size, 2.0–3.3×2.5–3.7 μm. The apex is narrowly grown with zigzag shape depending on formation of conidiophores to the length of 12–20 μm. Conidiophore is budded on the small spike (approximately 1 μm.) and is spherical or wide ellipsoidal, sometimes spiky base with size, 1.8–2.5×2.5–3.3 μm.

2. Culturing Properties on Various Media

Macroscopic observations of the strain cultured at 25° C. for 14 days are shown hereinbelow. On the following media, no formation of sclerotia or sclerotium-like structure is observed.

| Growth condition on medium (diameter of colony) | color tone of surface of colony | Color tone of everse of colony | Soluble pigment |
|---|---|---|---|
| Medium | | | |
| Potate glucose agar | | | |
| Good (40 mm) Floccose, plane, partly ridged penumbra, smooth penumbra | White | Pale yellowish white | None |
| Cornmeal agar | | | |
| Good (54 mm) Floccose, plane, tangled thread-like penumbra | White | Pale yellowish white-pale orange | None |
| Malt extract agar | | | |
| Good (32 mm) Floccose, ridged center, smooth penumbra | White | Pale brown | None |
| Miura agar | | | |
| Good (60 mm) powdery, plane, smooth penumbra | White | White | None |
| Yeast extract soluble starch agar | | | |
| Good (53 mm) velvety, ridged, smooth penumbra | White | Pale yellowish white-pale orange | None |

3. Physiological and Ecological Properties (1) Optimum Growth Condition:

Optimum growth condition of this strain is pH 4–7 at 15–30° C.

(2) Growth Range:

Growth range of this strain is pH 4–10 at 11–32° C.

(3) Differentiation of aerobic and unaerobic growth: aerobic

According to the above mentioned taxonomical properties, culturing properties and physiological properties of this strain FO-6979, the strain was compared with known microorganism strains. This strain was identified as the strain belonging to genus *Beauveria*, and was referred to *Beauveria* sp. FO-6979. This strain was deposited in Mar. 18, 1998 in the National Institute of Bioscience and Human-Technology, Higashi 1-1-3, Tsukuba-shi, Ibaraki-ken, Japan as the depository number FERM P-16716. This strain was later accepted the request for transfer based on the Budapest Treaty from the original depository in Mar. 16, 1999 by International Patent Organism Depository, National Institute of Advanced Industrial Science and Technology, AIST Tsukuba Center 6, 1-1, Higashi 1-Chome, Tsukuba-shi, Ibaraki-ken, 305-8566 Japan. The permanent depository number is FERM BP-6681.

Preferable example of FO-6979 substance producing strain used in the present invention is the strain *Beauveria* sp. FO-6979 herein-before mentioned. As is well known, the taxonomical properties of microorganisms are generally very easily changed by mutation and are not constant, and are easily mutated by natural or conventional artificial mutation techniques such as ultraviolet irradiation or use of mutagenic agent, e.g. N-methyl-N'-nitro-N-nitrosoguanidine, ethyl methanesulfonate, etc. Consequently, all strains belonging to genus *Beauveria* and having ability to produce FO-6979-M0 substance, -M1 substance, -M2 substance, -M3 substance and -M4 substance, including such artificial mutant strains and natural mutant strains, can be used in the present invention. In addition, all strains belonging to genus *Beauveria* and having ability to produce FO-6979-M0 substance, -M1 substance, -M2 substance, -M3 substance and -M4 substance, including strains mutated by cell engineering technology such as cell fusion, gene manipulation, etc., can be used in the present invention.

In practice of the present invention, at first, FO-6979 substance producing strain belonging to genus *Beauveria* is cultured in a medium. Nutrient sources preferably used for production of the above-mentioned FO-6979-M0 substance, -M1 substance, -M2 substance, -M3 substance and -M4 substance are assimilable carbon sources for microorganism, digestible nitrogen sources and, if necessary inorganic salts and vitamins can be used as nutritional medium.

Examples of carbon sources are sugars such as glucose, fructose, maltose, lactose, galactose, dextrin and starch and vegetable oils such as soybean oil, and are used independent or in combination.

Examples of nitrogen sources are peptone, yeast extract, meat extract, soybean powder, cotton seed powder, corn steep liquor, malt extract, casein, amino acids, urea, ammonium salts and nitrates, and are used independent or in combination. If necessary, salts such as phosphate, magnesium, calcium, sodium and potassium, heavy metal salts such as iron, manganese, copper, cobalt and zinc, vitamins and other materials preferable for production of FO-6979-M0 substance, -M1 substance, -M2 substance, -M3 substance and -M4 substance are optionally added.

In the culture, anti-foaming agents such as liquid paraffin, animal oil, vegetable oil, silicone, surface active agents, etc. can be added if necessary when foaming occurs. The culture can be performed by liquid or solid culture if containing the above nutrient sources, and generally the culture is preferable performed by the liquid culture. In the small culture, the culture using flask is preferable. In the large scale production using the large tank, in order to prevent delay of growth of microorganism in the production process, the production strain is inoculated and cultured initially in relatively small amount of culture medium, subsequently the cultured mass is transferred into the large tank and the cultivation is preferable continued. In this case, compositions of the medium used in the pre culture and the medium used in the production culture can be identical or different if necessary.

In the culture under aeration stirring condition, conventional means, for example, agitation using propeller and other mechanical stirring, rotation or shaking in fermenter, treating with pumping and blowing air can be applied. Air for aeration should be sterilized. Culturing temperature can be applied within ranges in the production of FO-6979-M0 substance, -M1 substance, -M2 substance, -M3 substance and -M4 substance by FO-6979 substance producing strain, and the cultivation is performed usually at 20–30° C., preferably at 27° C. Culturing pH is usually 5–8, preferably about pH 7. Culturing temperature depends on culturing condition and is usually for 10–20 days.

The thus obtained FO-6979-M0 substance, -M1 substance, -M2 substance, -M3 substance and -M4 substance exist in the cultured microorganism cells and the culture filtrate. Isolation of FO-6979-M0 substance, -M1 substance, -M2 substance, -M3 substance and -M4 substance from the cultured mass can be performed by extracting the whole cultured mass with water miscible organic solvent such as aceton, distilling off the organic solvent from the extract in vacuo, and extracting the residue with water immiscible organic solvent such as ethyl acetate. In addition to the above extraction procedure, conventional methods used for isolation of fat-soluble substances such as adsorption chromatography, gel filtration chromatography, thin-layer chromatography, counter current chromatography and high performance liquid chromatography can be used optionally in combination or repeatedly to isolate and purify FO-6979-M0 substance, -M1 substance, -M2 substance, -M3 substance and -M4 substance. Physicochemical properties of FO-6979 substances of the present invention are explained hereinbelow.

Figure 1:
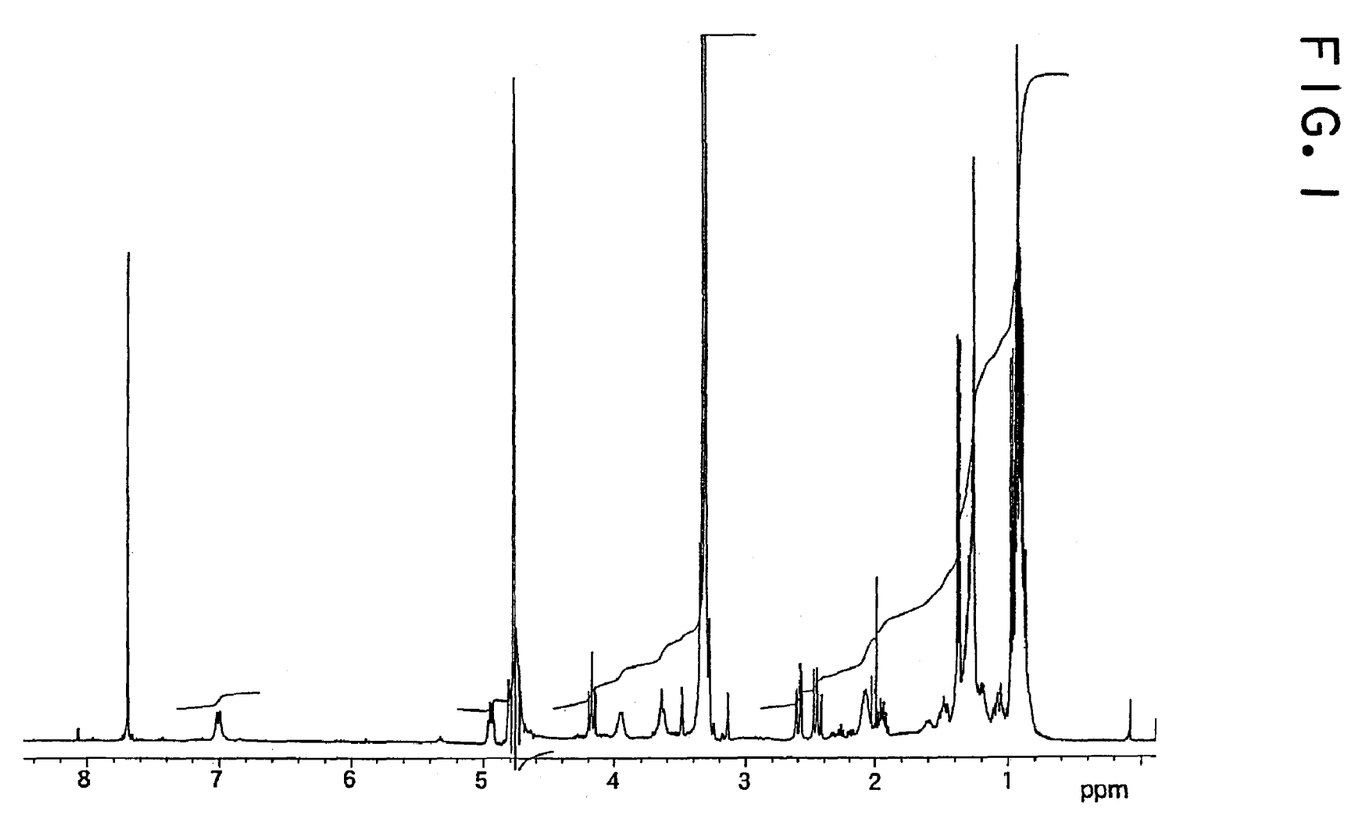
FIG. 1 is $^1$H-proton nuclear magnetic resonance spectrum (deuteriochloroform:deuteriomethanol=1:2) of FO-6979-M0 substance.

1. FO-6979-M0 Substance
 (1) Nature: white powder.
 (2) Melting point: 244–246° C.
 (3) Molecular formula: $C_{22}H_{39}N_3O_5$, FAB-MS (m/z): 426 [M+H]$^+$, 448 [M+Na]$^+$, HRFAB-MS (m/z) MF+Na, $C_{22}H_{39}N_3O_5Na$, Calculated: 448.27873, Found: 448.2787.
 (4) Molecular weight: 425 (fast atom bombardment mass spectrometry).
 (5) Ultraviolet spectrum: maximum absorption, λmax 209 nm ($CH_3OH$, log ε=18216).
 (6) Infrared spectrum (KBr Tablet): maximum absorption, vmax 1535, 1639, 1683, 1724 cm$^{-1}$.
 (7) Specific rotation: $[\alpha]_D^{23}$=-44° (c=0.41, chloroform:methanol=2:1).
 (8) Solubility in solvent: soluble in methanol, benzene, chloroform and ethyl acetate. slight soluble in water and hexane.
 (9) Color reaction: positive for sulfuric acid and phosphormolybdic acid.
 (10) Grouping for acidic, neutral and basic: Neutral substance.
 (11) $^1$H-nuclear magnetic resonance spectrum [XL-400 (Varian Inc., Japan) was used for measurement. Solvent: deuteriochloroform:deuteriomethanol=1:2]: As shown in FIG. 1.
 (12) $^{13}$C-nuclear magnetic resonance spectrum [XL-400 (Varian Inc., Japan) was used for measurement. Solvent: deuteriochloroform:deuteriomethanol=2:1]: Two signals at 13.4, 14.6, 15.0, 18.2, 18.4, 18.5, 18.7, 22.5, 27.7, 29.1, 30.1, 30.4, 35.1, 35.4, 49.2, 60.2, 62.1, 76.3, 169.0, 171.4, 171.8 and 171.9 ppm.

As described hereinabove, as the results of examining various physicochemical properties and spectral data of the present FO-6979-M0 substance, FO-6979-M0 substance was determined as having chemical structure represented by the formula [I]

[I]

Figure 2:
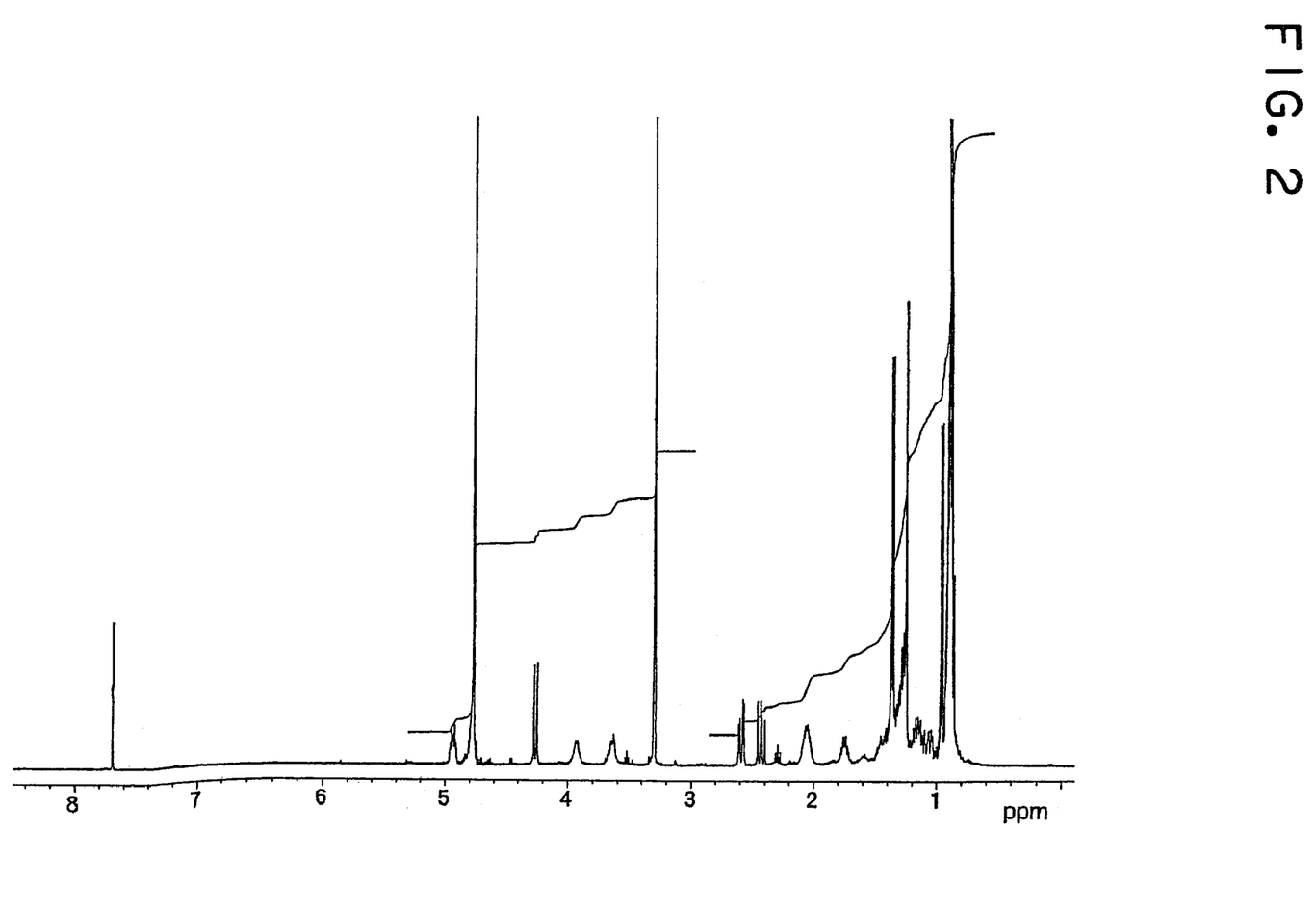
FIG. 2 is $^1$H-proton nuclear magnetic resonance spectrum (deuteriochloroform:deuteriomethanol=1:2) of FO-6979-M1 substance.

2. FO-6979-M1 Substance
 (1) Nature: white powder.
 (2) Melting point: 240–242° C.
 (3) Molecular formula: $C_{23}H_{41}N_3O_5$, FAB-MS (m/z): 440 [M+H]$^+$, 462 [M+Na]$^+$; HRFAB-MS (m/z) MF+Na, $C_{23}H_{41}N_3O_5Na$, Calculated: 462.29438, Found: 462.2944.
 (4) Molecular weight: 439 (fast atom bombardment mass spectrometry).
 (5) Ultraviolet spectrum: maximum absorption, λmax 208 nm ($CH_3OH$, log ε=24100).
 (6) Infrared spectrum (KBr Tablet): maximum absorption, vmax 1537, 1639, 1681, 1724 cm$^{-1}$.
 (7) Specific rotation: $[\alpha]_D^{23}$=-37° (c=0.5, chloroform:methanol=2:1).
 (8) Solubility in solvent: soluble in methanol, benzene, chloroform and ethyl acetate. slightly soluble in water and hexane.
 (9) Color reaction: positive for sulfuric acid and phosphormolybdic acid.
 (10) Grouping for acidic, neutral and basic: Neutral substance.
 (11) $^1$H-nuclear magnetic resonance spectrum [XL-400 (Varian Inc., Japan) was used for measurement. Solvent: deuteriochloroform:deuteriomethanol=1:2]: As shown in FIG. 2.
 (12) $^{13}$C-nuclear magnetic resonance spectrum [XL-400 (Varian Inc., Japan) was used for measurement. Solvent: deuteriochloroform:deuteriomethanol=1:2]: Twenty-three signals at 10.5, 13.6, 14.3, 14.7, 15.1, 18.7, 18.9, 23.0, 25.9, 28.2, 29.6, 29.8, 30.5, 35.7, 35.8, 37.0, 49.6, 59.5, 76.8, 169.6, 172.1, 172.3 and 172.6 ppm.

As described hereinabove, as the result of examining various physicochemical properties and spectral data of the present FO-6979-M1 substance, FO-6979-M1 substance was determined as having chemical structure represented by the formula [II]

[II]

3. FO-6979-M2 Substance
 (1) Nature: white powder
 (2) Melting point: 243–246° C.
 (3) Molecular formula: $C_{23}H_{41}N_3O_5$, FAB-MS (m/z): 440 [M+H]$^+$, 462 [M+Na]$^+$, HRFAB-MS (m/z) MF+H, $C_{23}H_{42}N_3O_5$, Calculated:440.31242, Found: 440.3124.
 (4) Molecular weight: 439 (fast atom bombardment mass spectrometry).
 (5) Ultraviolet spectrum: maximum absorption, λmax 209 nm ($CH_3OH$, log ε=15027).
 (6) Infrared spectrum (KBr Tablet): maximum absorption, vmax 1537, 1639, 1681, 1724 cm$^{-1}$.
 (7) Specific rotation: $[\alpha]_D^{25}$=-65° (c=0.47, chloroform:methanol=2:1).
 (8) Solubility in solvent: Soluble in methanol, benzene, chloroform and ethyl acetate. slightly soluble in water and hexane.

(9) Color reaction: positive for sulfuric acid and phosphormolybdic acid.

(10) Grouping for acidic, neutral and basic: Neutral substance.

Figure 3:
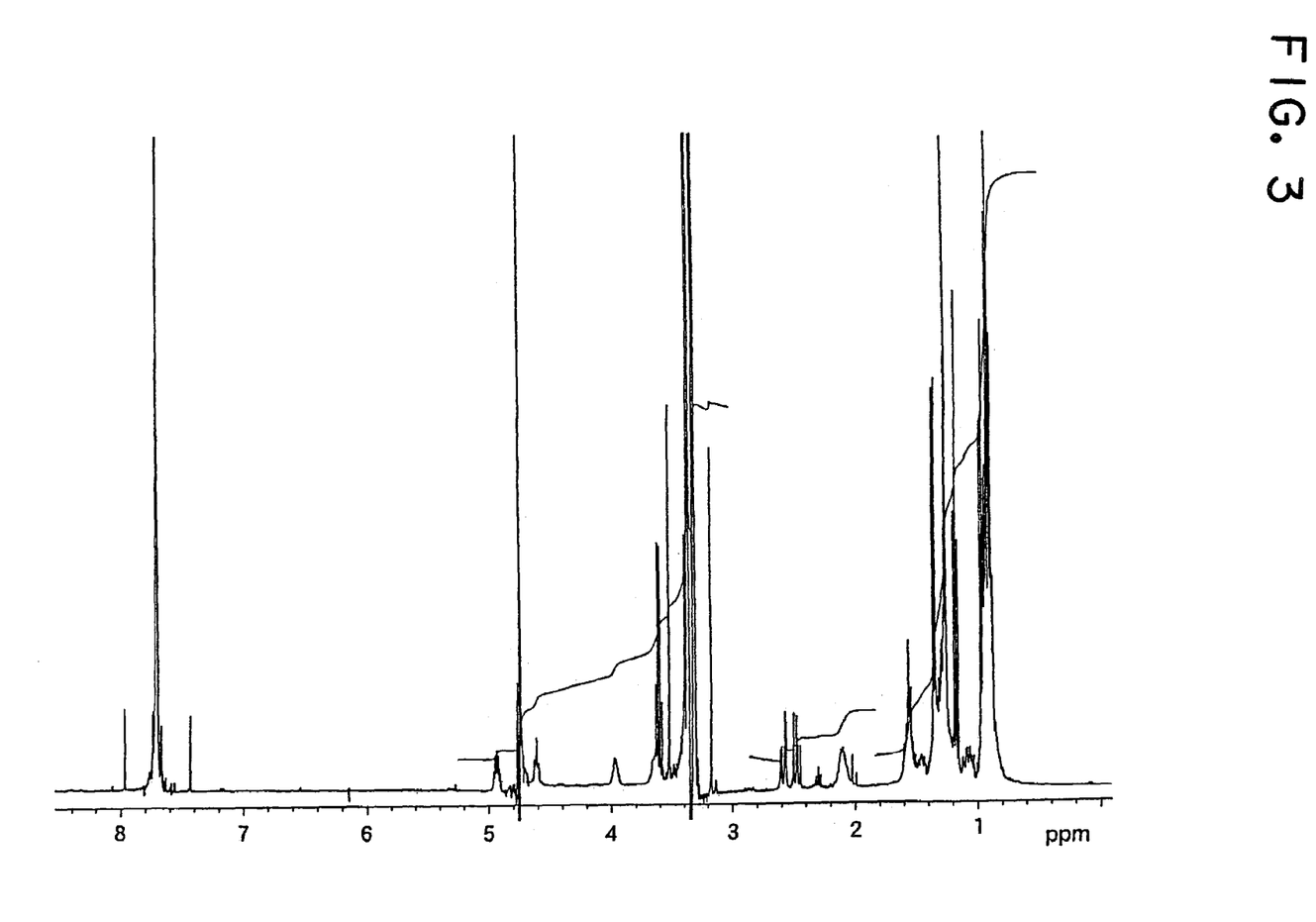
FIG. 3 is $^1$H-proton nuclear magnetic resonance spectrum (deuteriochloroform:deuteriomethanol=1:2) of FO-6979-M2 substance.

(11) $^1$H-nuclear magnetic resonance spectrum [XL-400 (Varian Inc., Japan) was used for measurement. Solvent: deuteriochloroform:deuteriomethanol=1:2]: As shown in FIG. 3.

(12) $^{13}$C-nuclear magnetic resonance spectrum [XL-400 (Varian Inc., Japan) was used for measurement. Solvent: deuteriochloroform:deuteriomethanol=1:2]: Two signals at 14.3, 15.6, 15.9, 19.4, 19.6, 22.6, 22.6, 23.7, 25.7, 29.0, 30.3, 30.4, 31.5, 36.4, 36.6, 41.9, 50.2, 53.5, 77.3, 170.7, 172.6, 173.2 and 173.2 ppm.

As described hereinabove, as the results of examining various physicochemical properties and spectral data of the present FO-6979-M2 substance. FO-6979 M2 substance was determined as having chemical structure represented by the formula [III]

[III]

4. FO-6979-M3 Substance (1) Nature: white powder.

(2) Melting point: 249–251° C.

(3) Molecular formula: $C_{26}H_{39}N_3O_5$, FAB-MS (m/z): 474 [M+H]$^+$, 496 [M+Na]$^+$; HRFAB-MS (m/z) MF+H, $C_{26}H_{40}N_3O_5$, Calculated: 474.29677, Found: 474.2968.

(4) Molecular weight: 473 (fast atom bombardment mass spectrometry).

(5) Ultraviolet spectrum: maximum absorption, λmax 209 nm (CH$_3$OH, log ε=28044)

(6) Infrared spectrum (KBr Tablet): maximum absorption, vmax 1537, 1639, 1687, 1726 cm$^{-1}$.

(7) Specific rotation: $[\alpha]_D^{23}$=–9.0 (c=0.20, chloroform: methanol=2:1).

(8) Solubility in solvent: soluble in methanol, benzene, chloroform and ethyl acetate slightly soluble in water and hexane.

(9) Color reaction: positive for sulfuric acid and phosphormolybdic acid.

(10) Grouping for acidic, neutral and basic: Neutral substance.

Figure 4:
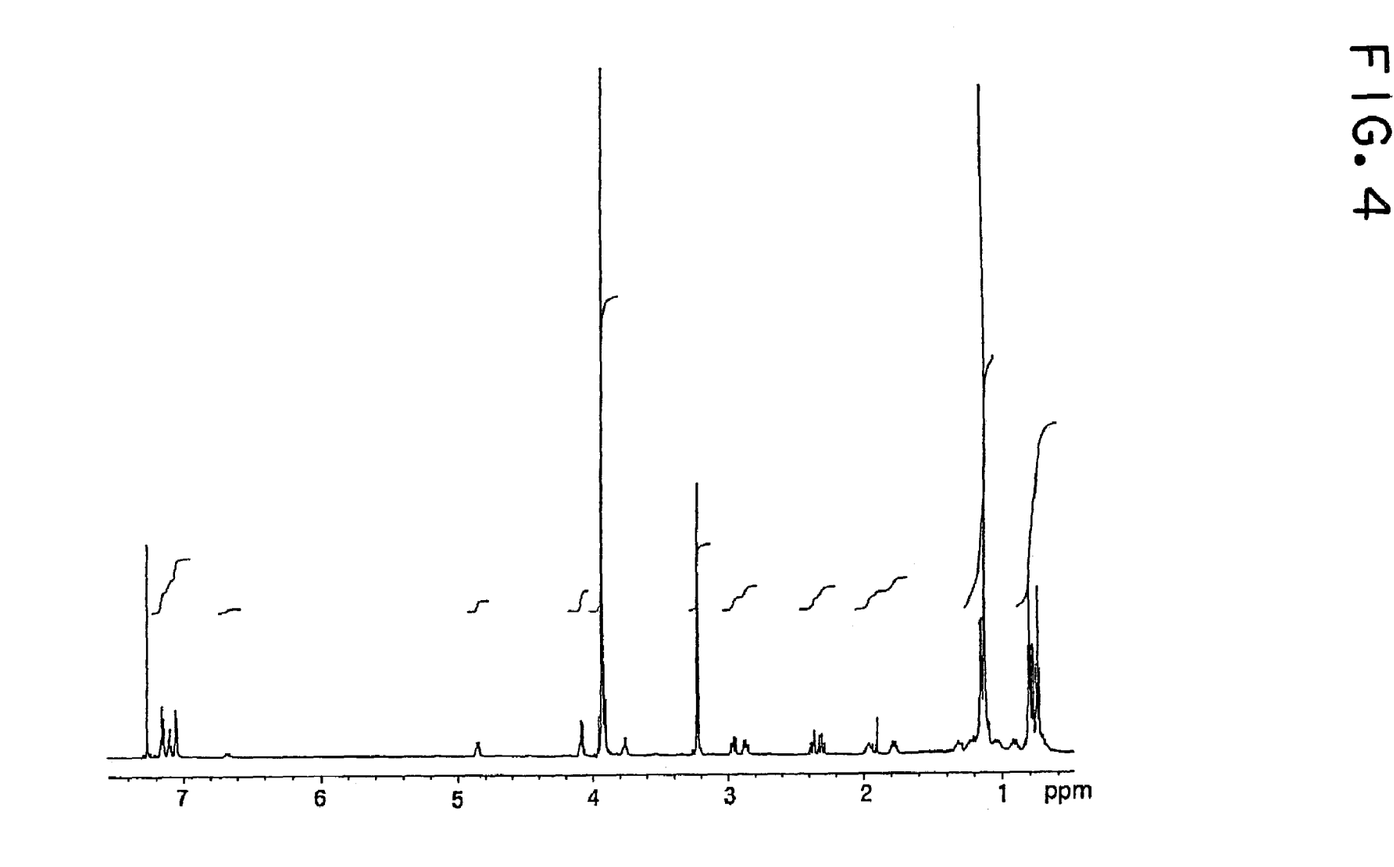
FIG. 4 is $^1$H-proton nuclear magnetic resonance spectrum (deuteriochloroform:deuteriomethanol=1:2) of FO-6979-M3 substance.

(11) $^1$H nuclear magnetic resonance spectrum [XL-400 (Varian Inc., Japan) was used for measurement. Solvent: deuteriochloroform:deuteriomethanol=4:1]: As shown in FIG. 4.

(12) $^{13}$C-nuclear magnetic resonance spectrum [XL-600 (Varian Inc., Japan) was used for measurement. Solvent: deuteriochloroform:deuteriomethanol=4:1]: Twenty-four signals (26 carbons) at 13.6, 14.6, 15.2, 18.4, 18.6, 22.6, 29.2, 30.3, 30.6, 35.3, 35.4, 35.7, 49.2, 56.8, 60.3, 76.3, 126.7, 128.3 (2 carbons), 128.8 (2 carbons), 136.2, 169.1, 171.3, 171.9 and 183.5 ppm.

As described hereinabove, as a result of examining various physicochemical properties and spectral data of the present FO-6979-M3 substance, FO-6979-M3 substance was determined as having chemical structure represented by the formula [IV]

[IV]

5. FO-6979-M4 Substance (1) Nature: white powder.

(2) Melting point: 244–246° C.

(3) Molecular formula: $C_{25}H_{45}N_3O_5$, FAB-MS (m/z): 468 [M+H]$^+$, 490 [M+Na]$^+$, HRFAB-MS (m/z) MF+H, $C_{25}H_{46}N_3O_5$, Calculated: 468.34372, Found: 468.3437.

(4) Molecular weight: 467 (fast atom bombardment mass spectrometry).

(5) Ultraviolet spectrum: maximum absorption, λmax 207 nm (CH$_3$OH, log ε=21400).

(6) Infrared spectrum (KBr Tablet): maximum absorption, vmax 1537, 1639, 1685, 1722 cm$^{-1}$.

(7) Specific rotation: $[\alpha]_D^{28}$=–45° (c=0.30, chloroform: methanol=2:1).

(8) Solubility in solvent: soluble in methanol, benzene, chloroform and ethyl acetate. slightly soluble in water and hezane.

(9) Color reaction: positive for sulfuric acid and phosphormolybdic acid.

(10) Grouping for acidic, neutral and basic: Neutral substance.

Figure 5:
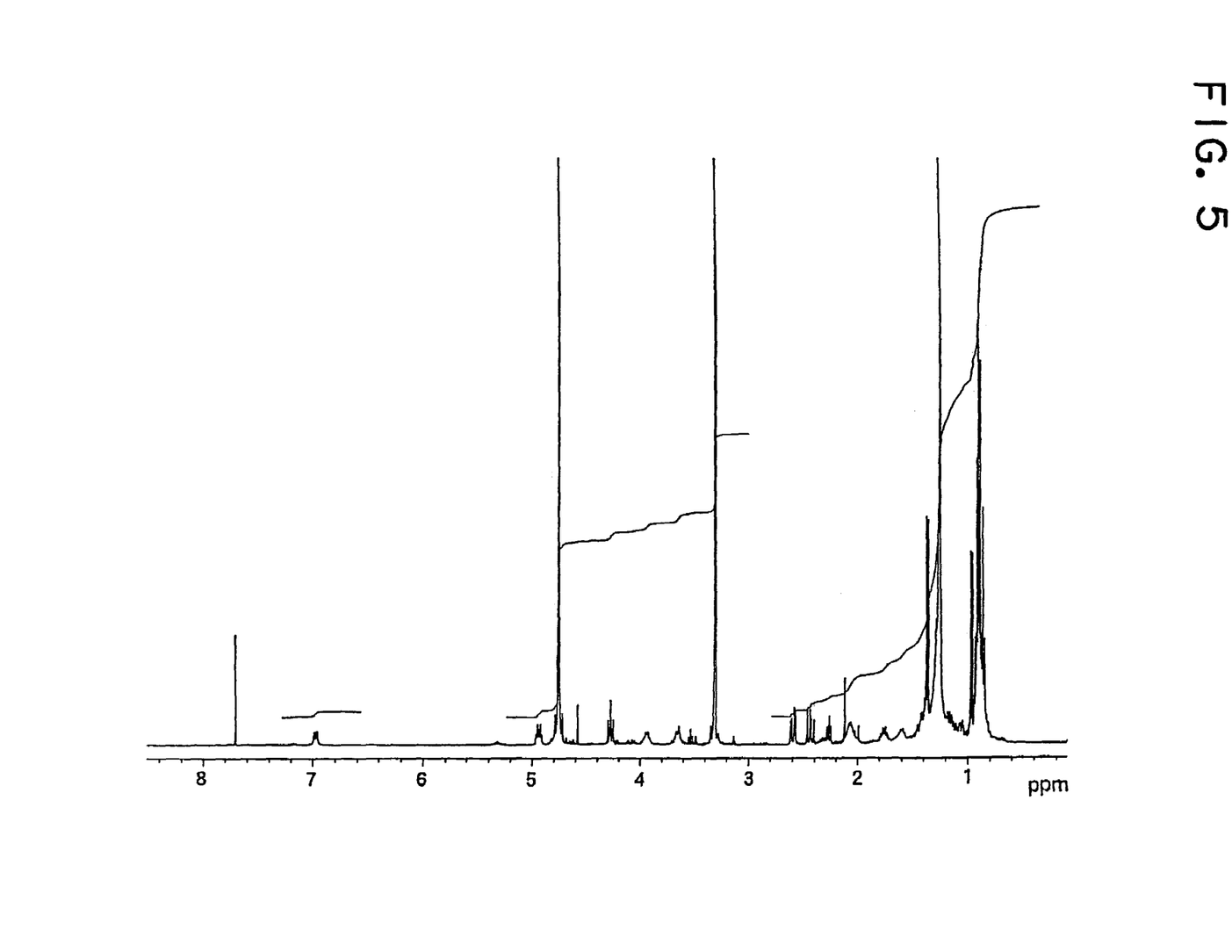
FIG. 5 is $^1$H-proton nuclear magnetic resonance spectrum (deuteriochloroform:deuteriomethanol=1:2) of FO-6979-M4 substance.

(11) $^1$H-nuclear magnetic resonance spectrum [XL-400 (Varian Inc., Japan) was used for measurement. Solvent: deuteriochloroform:deuteriomethanol=1:2]: As shown in FIG. 5.

(12) $^{13}$C-nuclear magnetic resonance spectrum [XL-400 (Varian Inc., Japan) was used for measurement. Solvent: deuteriochloroform:deuteriomethanol=1:2]: Twenty-five signals at 11.3, 14.3, 15.1, 15.5, 15.9, 19.4, 19.6, 23.3, 26.7, 28.2, 28.9, 30.4, 31.6, 32.6, 36.5, 36.6, 37.8, 50.4, 60.4, 62.8, 77.6, 170.3, 170.3, 173.1 and 173.4 ppm.

As described hereinabove, as a results of examining various physicochemical properties and spectral data of the present FO-6979-M4 substance. FO-6979-M4 substance was determined as having chemical structure represented by the formula [V]

[V]

Inhibitory activities of FO 6979-M0 substance, -M1 substance, -M2 substance, -M3 substance and -M4 substance of the present invention (hereinafter totally designates as FO-6979 substances) on acyl-CoA: cholesterol acyltransferase derived from mouse are explained hereinbelow.

Acyl-CoA: cholesterol acyltransferase activity was assayed by the modified method of Uelmen, et al. (J. Biol. Chem. 270: 26192–26201, 1995). A membrane fraction derived from mouse liver microsome was used as an enzyme origin. A mouse liver was homogenized with buffer A [50 mM Tris-HCL (pH 7.8), 1 mM EDTA and 1 mM phenylmethanesulfonyl fluoride] using Potter homogenizer (Tokyo-RIKO Inc.).

The homogenate was centrifuged at 12,000×g, and the supernatant solution was ultracentrifuged at 100,000×g to obtain the microsome fraction which was prepared for a solution with protein concentration 5 mg/ml by adding the buffer A. Assay of acyl-CoA: cholesterol acyltransferase activity was performed by adding enzyme 200 μg protein, 200 mM bovine serumu alubumin, [1-$^{14}$C] oleoyl-CoA (final concentration 170 μM, 0.09 μCi) and each FO-6979 substance into the buffer A to prepare total 100 μl solution and incubated at 37° C. for 10 minutes.

Subsequently, the reaction was terminated by adding 0.5 ml ethanol and added 1.5 ml hexane therein, then stirred well. Hexane layer 1 ml was dried up and was spotted on TLC plate (silica gel plate, thickness 0.5 mm, Merck Co., U.S.A.) which was developed with a solvent mixture, petroleum ether/diethyl ether/acetic acid (90:10:1, v/v). The generated [$^{14}$C] cholesteryl olate was quantitative measured using radio scanner (Ambis Co.). Results indicating concentration which inhibits 50% of Acyl-CoA: cholesterol acyltransferase activity of FO-6979 substances (-M0 substance~-M4 substance) (IC$_{50}$) are shown in the following table.

| Compound | IC$_{50}$ (μM) |
| --- | --- |
| FO-6979-M0 substance | >50 |
| FO-5979-M1 substance | >50 |
| FO-6979-M2 substance | 50 |
| FO-6979-M3 substance | 40 |
| FO-6979-M4 substance | 50 |

Inhibitory action of FO-6979 substances of the present invention on cholesteryl ester formation in mouse peritoneal macrophage is explained.

Cholesteryl ester formation and lipid droplets formation in mouse peritoneal macrophage were performed according to a method of Namatame et al.(J. Biochem. 125: 319–327, 1999). Macrophage isolated from mouse peritoneal fluid was suspended at 2.0×10$^6$ cells/ml in Dulbecco's modified Eagle's medium containing 6.8% lipoprotein deficient serum (6.8% LPDS-DMEM) and aliquots (0.25 ml) were dispensed into a 48-well microplate (Corning Co.).

The plate was incubated in a humidified 5% CO$_2$ atmosphere incubator at 37° C. for 2 hours, after which each plate was washed with Hank's solution to remove the unattached cells. The plate was incubated in 6.8% LPDS-DMEM for 1 hour, and each one of FO-6979 substances (2.5 μl 1 methanol solution), liposome [consisting of phosphatidylcholine/phosphatidylserine/dicetylphosphate/cholesterol=10:10:2:15 (nmol) in 10 μl of 0.3 M glucose] and [1-$^{14}$C] oleic acid (5 μl, 0.05 μCi, 1 nmol) were added therein, then incubated further 14 hours.

After the incubation, supernatant was removed and the intracellular neutral lipids were extracted twice with adding hexane 0.6 ml and isopropanol 0.4 ml. The mixture was concentrated, spotted on TLC plate (silica gel plate, Merck Co., thickness 0.5 mm) and developed and with a mixed solvent of hexane/diethyl ether/acetia acid(70:30:1, v/v). The separated [$^{14}$C] cholesteryl olate and [$^{14}$C] triacylglycerol were quantitatively assayed using radio scanner (Ambis Co.). Results indicated that generation of [$^{14}$C] cholesteryl olate was selectively inhibited and IC$_{50}$ value is shown in the following table.

| Compound | IC$_{50}$ (μM) |
| --- | --- |
| FO-6979-M0 substance | >25 |
| FO-6979-M1 substance | >45 (20% inhibition at 45 μM) |
| FO-6979-M2 substance | >25 |
| FO-6979-M3 substance | 21 |
| FO-6979-M3 substance | >25 |

Inhibitory action of FO-6979 substances of the present invention on lipid droplets formation in mouse peritoneal macrophage is explained.

Lipid droplets formation in mouse peritoneal macrophage was performed according to the method of Namatame et al. (J. Biochem. 125:319–327, 1999). Macrophage isolated from mouse peritoneal fluid was suspended at 2.0×10$^6$ cells/ml in Dulbecco's modified Eagle's medium containing 6.8% lipoprotein deficient serum (6.8% LPDS-DMEM) and aliquots (0.25 ml) were dispensed into a slide chamber (Nunc Co.).

The chamber was incubated in a humidified 5% CO$_2$ atmosphere incubator at 37° C. for 2 hours, after which the chamber was washed with Hank's solution to remove the unattached cells. The chamber was incubated in 6.8% LPDS-DMEM for 1 hour, and FO-6979-M3 substance (2.5 μl methanol solution) and liposome [consisting of phosphatidylcholine/phosphatidylserine/dicetylphosphate/cholesterol=10:10:2:15 (nmol) in 10 μl of 0.3 M glucose] were added therein, then incubated further 14 hours.

The lipid droplets and nuclei were double stained with oilred O and hematoxylin, and observed by optical microscope (Olympus OpticalCo., Japan). Results indicated that lipid droplets accumulated in cytoplasm under 20 μM of FO-6979-M3 substance were decreased to about 50% as compared with no drug addition (control), and lipid droplets accumulation was decreased in about 10–20% when added under 40 μM of FO-6979-M0 substance, -M0 substance, -M1 substance,-M2 substance and -M4 substance.

Next, toxicity test of FO-6979 substances of the present invention was explained hereinbelow.

No toxicity of FO-6979-M0 substance, -M1 substance, -M2 substance, -M3 substance or -M4 substance was observed for growth of mouse peritoneal macrophage at the final concentration of 50 µM. No toxicity was noted when FO-6979-M0 substance, -M1 substance, -M2 substance, -M3 substance and -M4 substance was administered intraperitoneally in mice with 100 mg/kg.

As described hereinabove, FO-6979-M0 substance, -M1 substance, -M2 substance, -M3 substance and -4 substance of the present invention are low toxicity, showing specific inhibitory action against acyl-CoA:cholesterol acyltransferase and showing inhibitory action against lipid droplets formation in macrophage, consequently these are expected to be useful for prevention and treatment of diseases caused by accumulation of cholesterol in human.

DETAILED DESCRIPTION OF PREFERRED EMBODIMENT

The following example illustrates the present invention, but is not construed to limit the invention.

A 500 ml Erlenmeyer flask containing a medium consisting of glucose 2.0%, polypeptone 0.5%, yeast extract 0.2%, $KH_2PO_4$ 0.1%, agar 0.1% and $MgSO_4.7H_2O$ 0.05% dissolved in tap water 100 ml (adjusted to pH 6.0) was cotton sealed and steam sterilized. Spore suspension ($10^7$ spores/ml) 100 µl of Beauveria sp. FO-6979 FERM BP-6681 grown on the agar medium was aseptically inoculated thereto and shake cultured at 27° C. for 3 days to obtain seed culture liquid.

A medium 20 lit. (adjusted to pH 6.7) consisting of glucose 1.0%, tryptone 0.5%, yeast extract 0.3% and agar 0.1% dissolved in tap water in 30 lit. jar fermenter (Mitsuwa Co., Japan) was steam sterilized and the above seed culture liquid 200 ml was aseptically inoculated thereto. This was cultured with agitation at 27° C. for 5 days. The cultured liquid 20 lit. was centrifuged at 10,000 rpm using KOKU-SAN Type S-6 ultracentrifuge (Kokusan Seiko Co.,Japan) to separate supernatant and mycelia. Mycelia were treated with acetone 18 lit. and filtered. The filtrate was concentrated in vacuo to obtain aqueous solution and precipitate. The precipitate was washed with 200 ml hexane to obtain insoluble crude substance 6 g. The substance was charged on a silica gel (600 g, silica gel 60, Merck Co., U.S.A.) column and gradually eluted stepwise with each 3.6 lit. of chloroform-methanol (100:0, 100:1, 100:2, 100:3 and 0:100).

Eluted chloroform-methanol fraction (100:2) containing FO-6979-M1 component, -M2 component and -M4 component was collected and dried in vacuo to obtain white substance 168 mg. Each substance was repeatedly purified using preparative HPLC [Apparatus: RANIN Co. ModelSD-200, Column: Shiseido CAPCELL-PAC C18 UG (20×250 mm), Detection: UV 210 nm, Flow rate: 6 ml/min., Elution: linear gradient with 50% aqueous acetonitrile up to 50 minutes, later 75% aqueous acetonitrilefor 25 minutes]. FO-6979-M1 substance 47.6 mg was eluted at the peak with retention time of 45 minutes, FO-6979-M2 substance 44.5 mg was eluted at the peak with retention time of 49 minutes and FO-6979-M4 substance 27.2 mg was eluted at the peak with retention time of 77 minutes.

A medium 20 lit. (adjusted to pH 6.7) consisting of glucose 1.0%, tryptone 0.5%, yeast extract 0.3%, malt extract 0.3% and agar 0.1% dissolved in tap water in 30 lit. jar fermenter (Mitsuwa Co., Japan) was steam sterilized and the above seed culture liquid 200 ml was aseptically inoculated thereto, and then the culture was initiated with agitation at 27° C. After 24 hours, aqueous L-valine solution, which was sterilized by filtration, was aseptically added to the cultured liquid up to final concentration at 0.3%. This was further cultured with agitation at 27° C. for 4 days. The thus obtained cultured liquid 20 lit. was centrifuged to obtain mycelia. Mycelia were treated with acetone and filtered. The filtrate was concentrated in vacuo to obtain precipitate. The precipitate was washed with 200 ml hexane to obtain insoluble crude substance 1.8 g. The substance was charged on a silica gel (180 g, silica gel 60, Merck Co., U.S.A.) column and gradually eluted stepwise with each 1.1 lit. of chloroform-methanol (100:0, 100:1, 100:2, 100:3 and 0:100).

The eluted fraction containing mainly of FO-6979-M3 component [the first half of eluate from chloroform-methanol (100:2) elution] and the eluted fraction containing mainly FO-6979-M0 component [the later half of eluate from chloroform-methanol (100:2) elution] were collected and dried in vacuo to obtain white substances, 100 mg and 357 mg respectively. Each substance was repeatedly purified using HPLC [Apparatus: RANIN Co. Model SD-200, Column: Shiseido CAPCELL-PAC C18 UG (20×250 mm), Detection: UV 210 nm, Flow rate: 6 ml/min., Elution:linear gradient with 50% aqueous acetonitrile up to 50 minutes, later75% aqueous acetonitrile for 25 minutes]. FO-6979-M0 substance 182 mg was eluted at the peak with retention time of 27 minutes. FO-6979-M3 substance 10.5 mg was eluted at the peak with retention time of 52 minutes.

INDUSTRIAL APPLICABILITY

As described hereinabove, FO-6979-M0 substance, -M1 substance, -M2 substance, -M3 substance and -M4 substance of the present invention are low toxicity, showing specific inhibitory action againstacyl-CoA: cholesterol acyltransferase, inhibitory action against cholesteryl esther and inhibitory action against lipid droplets formation in macrophage, consequently these are expected to be useful for prevention and treatment of diseases caused by accumulation of cholesterol in human.

What is claimed is:

1. An isolated FO-6979-M0 substance which is a compound represented by the following formula [I]

[I]

2. A process for production of novel FO-6979-M0 substance comprising culturing a microorganism *Beauveria* FO-6979 FERM BP-6681 having ability to produce FO-6979-M0 substance in a liquid medium, accumulating FO-6979-M0 substance in the cultured liquid medium and isolating FO-6979-M0 substance from the cultured mass.

3. The isolated FO-6979-M0 substance according to claim 1 which has inhibitory action against acyl-CoA: cholesterol acyltransferase.

4. The isolated FO-6979-M0 substance according to claim 1 which has inhibitory action against formation of cholesteryl ester.

5. The isolated FO-6979-M0 substance according to claim 1 which has inhibitory action against lipid droplet formation in macrophages.

6. An isolated FO-6979-M1 substance which is a compound represented by the following

[II]

7. A process for production of novel FO-6979-M1 substance comprising culturing a microorganism *Beauveria* FO-6979 FERN BP-6681 having ability to produce FO-6979-M1 substance in a liquid medium, accumulating FO-6979-M1 substance in the cultured liquid medium and isolating FO-6979-M1 substance from the cultured mass.

8. The isolated FO-6979-M1 substance according to claim 6 which has inhibitory action against acyl-CoA: cholesterol acyltransferase.

9. The isolated FO-6979-M1 substance according to claim 6 which has inhibitory action against formation of cholesteryl ester.

10. The isolated FO-6979-M1 substance according to claim 6 which has inhibitory action against lipid droplet formation in macrophages.

11. An isolated FO-6979-M2 substance which is a compound represented by the following formula [III]

[III]

12. A process for production of novel FO-6979-M2 substance comprising culturing a microorganism belonging to genus *Beauveria* having ability to produce FO-6979-M2 substance in a liquid medium, accumulating FO-6979-M2 substance in the cultured liquid medium and isolating FO-6979-M2 substance from the cultured mass, wherein the microorganism is *Beauveria* sp. FO-6979 FERN BP-6681.

13. The isolated FO-6979-M2 substance according to claim 11 which has inhibitory action against acyl-CoA: cholesteryl acyltransferase.

14. The isolated FO-6979-M2 substance according to claim 11 which has inhibitory action against formation of cholesteryl ester.

15. The isolated FO-6979-M2 substance according to claim 11 which has inhibitory action against lipid droplet formation in macrophages.

16. An isolated FO-6979-M3 substance which is a compound represented by the following formula [IV]

[IV]

17. A process for production of novel FO-6979-M3 substance comprising culturing a microorganism belonging to genus *Beauveria* having ability to produce FO-6979-M3 substance in a liquid medium, accumulating FO-6979-M3 substance in the cultured liquid medium and isolating FO-6979-M3 substance from the cultured mass, wherein the microorganism is *Beauveria* sp. FO-6979 FERN BP-6681.

18. The isolated FO-6979-M3 substance according to claim 16 which has inhibitory action against acyl-CoA: cholesterol acyltransferase.

19. The isolated FO-6979-M3 substance according to claim 16 which has inhibitory action against formation of cholesteryl ester.

20. The isolated FO-6979-M3 substance according to claim 16 which has inhibitory action against lipid droplet formation in macrophages.

21. An isolated FO-6979-M4 substance which is a compound represented by the following formula [V]

[V]

22. A process for production of novel FO-6979-M4 substance comprising culturing a microorganism belonging to genus *Beauveria* having ability to produce FO-6979-M4 substance in a liquid medium, accumulating FO-6979-M4 substance in the cultured liquid medium and isolating FO-6979-M4 substance from the cultured mass, wherein the microorganism is *Beauveria* sp. FO-6979 FERN BP-6681.

23. The isolated FO-6979-M4 substance according to claim 21 which has inhibitory action against acyl-CoA: cholesyerol acyltransferase.

24. The isolated FO-6979-M4 substance according to claim 21 which has inhibitory action against formation of cholesteryl ester.

25. The isolated FO-6979-M4 substance according to claim 21 which has inhibitory action against lipid droplet formation in macrophages.

* * * * *